United States Patent [19]

Downing et al.

[11] 4,125,483

[45] Nov. 14, 1978

[54] DIMERIZATION PROCESS CATALYST

[75] Inventors: Roger S. Downing; Jan van Amstel; Annie H. Joustra, all of Amsterdam, Netherlands

[73] Assignee: Shell Oil Company, Houston, Tex.

[21] Appl. No.: 797,277

[22] Filed: May 16, 1977

[51] Int. Cl.$^2$ .................. B01J 29/06; B01J 23/02
[52] U.S. Cl. ............................ 252/455 R; 252/476
[58] Field of Search ................ 252/476, 454, 455 Z, 252/455 R

[56] References Cited

U.S. PATENT DOCUMENTS

| 3,185,745 | 5/1965 | Lindsay | 252/476 X |
| 3,444,253 | 5/1969 | Reimlinger et al. | 252/455 Z |
| 3,962,136 | 6/1976 | Nielsen et al. | 252/476 X |

Primary Examiner—Carl Dees

[57] ABSTRACT

An improved catalyst for the dimerization of butadiene to 4-vinylcyclohexene comprises a cation-exchangeable alumino silicate having incorporated in the lattice thereof by the exchange Cu(I) ions and alkali metal ions, preferably cesium ions.

3 Claims, No Drawings

DIMERIZATION PROCESS CATALYST

BACKGROUND OF THE INVENTION

1. Field of the Invention

This invention relates to a process for the catalytic dimerization of butadiene to 4-vinylcyclohexene.

2. Prior Art

It is known from U.S. Pat. No. 3,444,253 that copper(I) zeolites may be used as catalysts for the dimerization of butadiene. A disadvantage associated with the use of such catalysts is that they undergo a significant deactivation with time due to the formation of polymeric material on the surface of the catalyst.

SUMMARY OF THE INVENTION

The process of the present invention uses a new catalyst which gives rise to a reduced formation of polymeric material and hence exhibits a lower rate of deactivation.

Accordingly the invention provides a process for catalytically dimerizing butadiene to 4-vinylcyclohexene, in which the catalyst is a cation-exchangeable aluminosilicate into which copper(I) ions and ions of an alkali metal having an atomic number of at least 19, preferably cesium, have been introduced.

DESCRIPTION OF THE PREFERRED EMBODIMENTS

By the term "cation-exchangeable aluminosilicate" is meant a substance having a macromlecular of aluminum, silicon and oxygen atoms, in which one cationic constituent can be replaced by another by treatment with a compound containing the other cation. Examples of such aluminosilicates are natural and synthetic zeolites such as a faujasite, clay minerals such as montmorillonite and synthetic silica/aluminas.

The copper(I) and alkali metal ions may be introduced into the aluminosilicate by any of the known methods used for exchanging cations in aluminosilicates. The copper(I) ions may be introduced from either aqueous or non-aqueous solution. A preferred method is by contacting the aluminosilicate with an aqueous solution containing copper(I) ions complexed with a suitable ligand, for example, a nitrogen-containing ligand such as ammonia. Alternatively copper(II) ions may be first introduced and then reduced to copper(I) ions. The alkali metal ions are preferably introduced by contacting the aluminosilicate with an aqueous solution of a water-soluble salt of the alkali metal. The order in which the ions are introduced into the aluminosilicate is not critical and it is even possible to introduce the copper(I) and alkali metal ions simultaneously.

The weight of copper and alkali metal introduced as ions into the aluminosilicate will depend on the cation exchange capacity of the aluminosilicate. Typically up to 5%w of each type of ion, based on the weight of aluminosilicate, may be introduced. After the introduction of the ions the catalyst is preferably calcined under nitrogen at 200°–400° C. before being used.

The starting material for the process may be pure butadiene, or alternatively a commercially available mixture containing ca 40% butadiene togeher with butanes and butenes.

The process of the invention may be carried out using the known procedure for catalytic conversations. Thus, the butadiene, either in gaseous or liquid state, and optionally in admixture with a gaseous or liquid diluent, for example nitrogen or an alkane, may be passed over the catalyst at 20° to 200° C., preferably 80° to 120° C., and at atmospheric or superatmospheric pressure, for example 10 to 30 bar. The vinylcyclohexene may be recovered from the reaction mixture by conventional methods, for example, by distillation.

The invention is illustrated further in the following Illustrative Embodiments which are provided for illustration and are not to be construed as limiting the invention.

ILLUSTRATIVE EMBODIMENTS

EXAMPLE I (a) A montmorillonite clay (Sud Chemie, 30 g) was stirred with a 0.5 M cesium sulphate solution (220 ml) for 6 hours at room temperature and then filtered off, washed with deionized water and dried at 120° C. The clay was then stirred for two hours under nitrogen with a copper(I) solution formed by mixing hydrated copper sulphate, 25% aqueous ammonia solution and 20% hydrazine hydrate solution in oxygen-free distilled water. The catalyst was finally washed with oxygen-free deionized water and dried under nitrogen at 80° C. The catalyst contained 1.79%w cesium and 1.6%w copper based on the weight of clay.

(b) The catalyst prepared as in (a) was activated by heating at 300° C. in a nitrogen stream for 16 hours. A 40%w solution of butadiene in n-pentane was then passed over the catalyst at 100° C., a pressure of 30 bar and at a total space velocity of one liter solution per liter of catalyst per hour. The product was examined by GLC and the initial conversion of butadiene and the selectivity towards vinylcyclohexene were determined. The results were

| Initial Conversion | 35% |
|---|---|
| Selectivity | 95% |

Comparitive Experiment A

The rate at which the percentage conversation achieved by the catalyst of Example I decreased with time was compared with the conversion decline for a similar catalyst containing 1.87%w copper and no cesium. The results were as follows:

| Catalyst | Conversion decline per hour, % |
|---|---|
| Example I | 0.018 |
| Montmorillonite/Cu(I) | 0.07 |

EXAMPLE II (a) A synthetic silica/alumina (Ketjen LA-HPO, 30 g) was converted to the sodium form by titration with 0.1 M sodium hydroxide to pH 7. It was then washed with deionized water, dried at 120° C. for 1 hour. The silica alumina was then treated with the cesium sulphate solution and the copper(I) solution as described in Example I(a). The catalyst so produced contained 1.95%w cesium and 2.5%w copper based on the weight of silica/alumina.

(b) The catalyst was activated and tested in a dimerization experiment as described in Example I(b). The results were

| Initial conversion of butadiene | 40% |
|---|---|

-continued

| | |
|---|---|
| Selectivity to vinylcyclohexene | 100% |

Comparative Experiment B

The rate at which the percentage conversion achieved by the catalyst of Example II decreased with time was compared with the conversion decline for a similar catalyst containing 2.22% copper and no cesium. The results were as follows:

| Catalyst | Conversion decline per hour, % |
|---|---|
| Example II | 0.09 |
| Silica/alumina/Cu(I) | 0.2 |

We claim as our invention:

1. A catalyst composition comprising a cation-exchangeable aluminosilicate selected from the group consisting of montmorillonite clay mineral and synthetic silica-alumina having incorporated in the lattice thereof by ion exchange from about 0.1 to about 5 percent by weight, basis aluminosilicate, of copper(I) ions and from about 0.1 to about 5 percent by weight, basis aluminosilicate, of ions of cesium.

2. The process of preparing the catalyst of claim 1 which comprises
   (a) contacting the aluminosilicate with an aqueous solution containing copper(I) ions complexed with a suitable nitrogen-containing ligand;
   (b) contacting the aluminosilicate with an aqueous solution of a water soluble salt of cesium metal, and
   (c) subsequently calcining the catalyst under nitrogen at about 200° C. to about 400° C.

3. The process of claim 2 wherein the nitrogen-containing ligand is ammonia and the alkali metal is cesium.

* * * * *